US005198353A

United States Patent [19]

Hawkins et al.

[11] Patent Number: 5,198,353

[45] Date of Patent: Mar. 30, 1993

[54] METHOD FOR PREPARING STABILIZED ENZYME DISPERSION

[75] Inventors: John Hawkins; Philip Chadwick; Edward T. Messenger, all of Cumbria, Great Britain; Mads Lykke, Copenhagen, Denmark

[73] Assignees: Novo Nordisk A/S, Novo Alle, Denmark; Albright & Wilson Limited, Warley, England

[21] Appl. No.: 634,890

[22] PCT Filed: Jul. 11, 1989

[86] PCT No.: PCT/DK89/00172

§ 371 Date: Jan. 28, 1991

§ 102(e) Date: Jan. 28, 1991

[87] PCT Pub. No.: WO90/00593

PCT Pub. Date: Jan. 25, 1990

[30] Foreign Application Priority Data

Feb. 11, 1988 [GB] United Kingdom ................. 8816443

[51] Int. Cl.$^5$ ........................ C12N 9/96; C11D 17/00

[52] U.S. Cl. ............................... 435/188; 252/174.12; 252/174.13; 252/174.14

[58] Field of Search ................... 435/188; 252/174.12, 252/174.13, 174.14

[56] References Cited

U.S. PATENT DOCUMENTS

| | | | |
|---|---|---|---|
| 3,557,002 | 1/1971 | McCarty | 252/174.12 |
| 3,627,688 | 12/1971 | McCarty et al. | 252/174.12 |
| 3,629,123 | 12/1971 | O'Reilly et al. | 252/174.12 |
| 3,634,258 | 1/1972 | Wildi et al. | 252/174.12 |
| 3,714,051 | 1/1973 | Milesi et al. | 252/132 |
| 3,723,250 | 3/1973 | Aunstrup et al. | 435/221 |
| 3,860,484 | 1/1975 | O'Malley | 435/188 |
| 3,860,536 | 1/1975 | Landwerden et al. | 435/188 |
| 4,090,973 | 5/1978 | Maguire, Jr. et al. | 252/89 |
| 4,203,857 | 5/1980 | Dugan | 252/134 |
| 4,250,255 | 2/1981 | Sanford | 435/4 |
| 4,526,698 | 7/1985 | Kuroda et al. | 252/174.13 |
| 4,707,287 | 11/1987 | Herdeman | 435/188 |
| 4,743,394 | 5/1988 | Kaufman et al. | 252/174.14 |
| 4,767,557 | 8/1988 | Herdeman | 435/188 |

FOREIGN PATENT DOCUMENTS

| | | |
|---|---|---|
| 0005131 | 10/1979 | European Pat. Off. . |
| 0253520 | 1/1988 | European Pat. Off. . |
| 0303062 | 2/1989 | European Pat. Off. . |
| 61-254244 | 11/1986 | Japan . |
| 63-105098 | 5/1988 | Japan . |
| 63-305198 | 12/1988 | Japan . |

*Primary Examiner*—Herbert J. Lilling
*Assistant Examiner*—Mike Meller
*Attorney, Agent, or Firm*—Steve T. Zelson; Elias J. Lambiris

[57] ABSTRACT

Disclosed is a method for preparing a stabilized enzyme dispersion wherein the dispersion is prepared by precipitating a water-soluble polymer from a single phase, aqueous solution to form an aqueous dispersion, and before, simultaneously with or after precipitating the polymer, contacting the dissolved or dispersed polymer with an aqueous solution or fine aqueous dispersion of an enzyme without any covalent bonding between the polymer and the enzyme. Also disclosed is a clear solution for use in the method.

17 Claims, No Drawings

METHOD FOR PREPARING STABILIZED ENZYME DISPERSION

This application is a continuation of Ser. No PCT/DK89/00172, filed Jul. 11, 1989.

TECHNICAL FIELD

The present invention relates to stabilized enzyme dispersions.

BACKGROUND ART

Ensuring sufficient enzyme stability during storage represents a problem in the formulation of liquid enzymatic systems such as liquid enzymatic detergents, particularly those containing a detergent builder The problem has received considerable attention in the prior art. One approach has been incorporation of various chemicals as enzyme stabilizers.

Another approach has been to coat or encapsulate the enzyme with a suitable coating agent and disperse the coated enzyme in the liquid detergent.

Thus, the method described in EP-A-0238216 entails dispersing enzymes as particles in liquid detergent which has a structure which prevents sedimentation of the particles, after coating the particles with a hydrophobic, water-insoluble substance such as a silicone which isolates the particles from the aggressive medium. U.S. Pat. No. 4,090,973 describes encapsulating the enzyme in a water-soluble, solid surface active agent, such as polyvinyl alcohol or polyethylene glycol before addition to the liquid detergent. JP-A 63-105,098 describes coating of enzymes with polyvinyl alcohol to form microcapsules and dispersing the capsules uniformly in a liquid detergent to improve storage stability.

The methods according to said publications involve physically surrounding a particle or droplet containing the enzyme with a barrier which isolates the enzyme more or less effectively from the detergent medium. To ensure effective coating or encapsulation of the enzyme with a protective material, a relatively high amount of the latter is required.

One method, described in EP-A 0,238,216, is to protect the enzyme by dispersing it in a hydrophobic liquid which is insoluble in the detergent, such as silicone oil, and dispersing the liquid in the detergent. Another proposed method is to encapsulate the enzyme in non-ionic surfactant (U.S. Pat. No. 4,090,973) or polyvinyl alcohol (GB 1,204,123, JP-A 63-105,098, FR 2,132,216) by physically coating solid particles of enzyme with the encapsulant. JP-A 61-254,244 describes dispersing an enzyme in an aqueous polymer solution, dispersing the latter in a hydrocarbon and precipitating the polymer to form the micro capsules

SUMMARY OF THE INVENTION

We have found that when water soluble polymers are precipitated from aqueous solution to form a dispersion in the water and either the precipitation is effected in the presence of dissolved or finely dispersed enzyme, or the precipitate is subsequently contacted with dissolved or finely dispersed enzyme, so as to form a codispersion in water of the enzyme and polymer, substantial improvement of the enzyme stability during storage can be obtained with surprisingly little polymer (relative to enzyme). Our observation that enzyme stabilization can, surprisingly, even be obtained by contacting precipitated polymer with dissolved enzyme, leads us to believe that the stabilizing effect is not due (or at least not primarily due) to encapsulation.

Our invention, therefore, provides a method for the preparation of a stabilized aqueous enzyme dispersion comprising:

(1) precipitating a water-soluble polymer from aqueous solution to form an aqueous dispersion, and (2) before, after or simultaneously with (1), contacting the dissolved or dispersed polymer with an aqueous solution or fine aqueous dispersion of enzyme.

A particularly preferred method comprises coprecipitation of enzyme and polymer from a solution comprising both of these or precipitation of the polymer in the presence of the dissolved enzyme. The stabilized enzyme dispersion according to the invention may in particular be an enzymatic liquid detergent or an enzymatic detergent additive.

DETAILED DESCRIPTION OF THE INVENTION

Enzyme

Typically the enzyme used in the invention is a protease, lipase, cellulase, amylase or other stain and/or soil removing enzyme. Mixtures of enzymes may be employed. For use in a liquid detergent the enzyme is preferably selected for stability at alkaline pH.

Polymer

The polymer to be used in the invention is preferably a water-soluble polymer that can be precipitated by electrolyte or organic solvent. This choice of polymer allows the enzyme to be released by diluting the enzyme dispersion with water.

We particularly prefer a water soluble polyvinyl pyrrolidone. We can also use a polyvinyl alcohol or a cellulose derivative such as carboxymethyl cellulose, methyl cellulose or hydroxypropyl cellulose, a gum such as guar gum, gum benzoin, gum tragacanth, gum arabic or gum acacia, a protein such as casein, gelatin or albumin, or polycarboxylates such as polyacrylates, polymaleates or copolymers of acrylate and methacrylate. For obvious reasons we prefer not to use protein to stabilize proteases or cellulose derivatives to stabilize cellulases.

Where polyvinyl pyrrolidone is used we prefer to use a polymer with a molecular weight of 1,000 to 1,500,000. For good stabilization we prefer molecular weights below 1,000,000, e.g. below 800,000, especially below 200,000 and most preferably below 100,000. We generally prefer to use molecular weights above 5,000, especially above 10,000, more particularly above 20,000, e.g. above 25,000.

In the case of polyvinyl alcohol we particularly prefer polymers with a molecular weight of 18,000 to 140,000, preferably 50,000 to 120,000, e.g. 80,000 to 100,000. Preferably any polyvinyl alcohol used according to our invention is a partially hydrolysed polyvinyl ester of a lower (e.g. $C_1$–$C_4$) carboxylic acid, especially polyvinyl acetate, which has a degree of hydrolysis of greater than 25%, and desirably less than 95%, especially 50 to 90%, more preferably 60 to 80%, e.g. 70 to 75%.

To obtain sufficient stabilization we generally prefer an amount of polymer corresponding to a weight ratio of polymer: enzyme (pure enzyme protein) above 0.03, e.g. above 0.1, especially above 0.4 and particularly above 1. If the polymer is used only for enzyme stabilization we prefer a polymer : enzyme ratio below 5, especially below 2, but a larger amount of polymer may be used if it also serves another function (e.g. PVA or CMC for antiredeposition in detergent).

Precipitation

The method of the invention for preparing an enzyme dispersion involves precipitation of a water soluble polymer to form an aqueous dispersion, which is preferably non-sedimenting. Coprecipitation of enzyme and polymer or precipitation of the enzyme in the presence of dissolved polymer are preferred embodiments.

In one preferred embodiment, the precipitation is effected by contacting a solution containing the polymer (and optionally the enzyme) with an effective amount of a precipitant. Conventional measures may be used to obtain a suitably small particle size to form a dispersion, e.g. slow addition of precipitant with agitation.

The precipitant may be an electrolyte, i.e. precipitation by salting out. Examples of suitable electrolytes are sodium sulphate, sodium citrate, sodium carbonate, sodium nitrilotriacetic acid, sodium tripolyphosphate, sodium nitrate, sodium borate and ammonium sulphate. Solid electrolyte or an electrolyte solution may be added to the polymer solution.

Alternatively, the precipitant may be an organic solvent. The solvent should be partly or fully miscible with water and should be able to precipitate the polymer. Examples of suitable solvents are, in the case of PVP: acetone, and in the case of PVA: acetone or ethanol.

In an alternative embodiment, the precipitation of the polymer (and optionally the enzyme) may be effected by evaporation of a solution, e g. an aqueous solution. Spray drying is preferred, e.g. the polymer may be dissolved in a concentrated aqueous solution of enzyme and the mixture spray dried.

In order to obtain a non-sedimenting dispersion of the water soluble polymer it is preferred that the precipitation of the polymer is effected in the presence of a dispersant. The dispersant may be a surfactant capable of maintaining the precipitated polymer in stable dispersion. In particular a structured surfactant formed by the interaction with electrolyte is preferably present. Alternatively solvents such as polyglycols, present in the enzyme solution, may act as the dispersant.

Contacting polymer with enzyme

A preferred embodiment of the invention comprises coprecipitation of enzyme and polymer, especially from a clear solution. Such a clear solution containing polyvinyl pyrrolidone as the polymer and a protease, an amylase, a cellulase or a lipase as the enzyme is novel and is provided by the invention.

Particularly advantageously, the coprecipitation may take place in situ by contacting the enzyme/polymer solution with a precipitant to directly form the stabilized enzyme dispersion. This reduces the cost of preparing the dispersion and gives a reliable stabilization.

As an alternative to in-situ preparation, the coprecipitated polymer and enzyme, formed e g. by precipitation by contacting with a precipitant or by evaporation, may be collected as a finely divided solid, e.g. by filtration or spray drying, optionally followed by comminution, e.g. by grinding. The solid coprecipitate can then be dispersed in liquid to form the stabilized enzyme dispersion.

Enzyme solutions for use in coprecipitation according to the preferred embodiment of our invention may conveniently contain 0.1-10% of enzyme (pure enzyme protein, by weight), especially 0.5-5%. The solution may contain up to 90%, by weight of the solution, of an enzyme stabilizing water-miscible organic solvent, especially a water-miscible alcohol or glycol such as propylene glycol or glycerol. The alcohol is preferably present in proportion of from 10 to 80% by weight of the solution, e.g. 25 to 75% by weight. Other enzyme stabilizers that may be present include lower mono- or dicarboxylic acids and their salts, such as formates, acetates and oxalates, borates and calcium salts. The solution typically contains from 0.5% to 10%, e.g. 1 to 5% by weight organic enzyme coating material We prefer, however, that the enzyme solution be substantially free of polyglycols which may tend to disperse the polymer used in the invention.

The solution of the polymer before coprecipitation may conveniently have a concentration of from 0.5% by weight of polymer (based on the weight of the solution) up to saturation. Preferably the concentration is sufficiently low for the enzyme and the polymer to be mixed to form a stable, clear, mobile mixed solution Concentrations from 1 to 20% of polymer, depending on the solubility are usually preferred, especially 2 to 10%, e.g. 3 to 6%, by weight of the solution.

A solution of enzyme and polymer suitable for use in preparing dispersions of the invention may be prepared by dissolving solid polymer in aqueous enzyme.

In the case of preparing a liquid detergent by coprecipitation, preferably a concentrated aqueous surfactant at substantially neutral pH and containing sufficient electrolyte to form a structured system is mixed with a solution of enzyme and polymer. Part of the electrolyte may optionally be premixed with the enzyme and polymer immediately (e.g. less than 2 minutes) prior to addition thereof to the surfactant. The resulting dispersion of enzyme and polymer may be stored and subsequently added to an alkaline aqueous liquid detergent, preferably together with alkaline and/or solid builders such as sodium tripolyphosphate and/or zeolite.

As an alternative to coprecipitation, precipitated, dispersed polymer may be contacted with dissolved enzyme. Or alternatively dissolved polymer may be contacted with finely divided solid (e.g dispersed) enzyme. These alternatives provide effective stabilization and may be convenient if the polymer or enzyme is available in solid form.

Enzyme dispersion

The stabilized enzyme dispersion according to the invention should have a high enough content of precipitant (e.g. electrolyte) to prevent complete dissolution of the dispersed particles of enzyme and polymer. The content of precipitant is not necessarily high enough to precipitate the enzyme in the absence of polymer.

The stabilized enzyme dispersion may additionally comprise stabilizers or activators for the enzyme. For example enzymes may be stabilized by the presence of calcium salts.

Depending on the intended use of the enzyme dispersion it may be desirable, or even essential, that the dispersion does not sediment during storage, but a sedimenting system may be acceptable if the sediment can be re-dispersed e.g. by stirring or shaking. A non-sedimenting system can be formulated according to principles known in the art.

As mentioned above, the invention is particularly amenable to the preparation of liquid enzymatic detergent and to preparation of liquid enzymatic detergent additive for use in liquid detergent.

A stabilized enzyme dispersion wherein the dispersed enzyme particles contain polyvinyl pyrrolidone or polycarboxylic acid is novel and is provided by the invention.

Enzymatic liquid detergent

In the case of a liquid detergent, the enzyme dispersion should preferably be non-sedimenting. The liquid detergent compositions may be of the type in which an electrolyte interacts with aqueous surfactant to form a structured dispersion of lamellar or spherulitic surfactant, as described in GB 2,123,846 or GB 2,153,380. The suspending properties of a structured liquid detergent assist in preventing the particles of enzyme and polymer from undergoing agglomeration and sedimentation. The electrolyte also prevents the dissolution of the water soluble particles. The latter protects the enzyme until the detergent is introduced into wash liquor, where the electrolyte is diluted sufficiently for the particle to dissolve and release the enzyme, so that it is available to act on stains. Physical shearing associated with washing may also contribute to the release of the enzyme.

Thus, preferably the liquid detergent composition comprises a surfactant desolubilising electrolyte, said electrolyte being present in a concentration at which said surfactant forms a structure capable of stably suspending the enzyme/polymer particles and sufficient to prevent or inhibit dissolution of the water soluble polymer. Typically, the polymer is a hydrophilic polymer which is soluble in dilute wash liquor but insoluble in concentrated liquid laundry detergent.

Preferably the dispersed enzyme is added to, or formed by precipitation in, a liquid detergent which comprises an aqueous phase, surfactant and sufficient electrolyte dissolved in the aqueous phase to form, with the surfactant, a structure capable of supporting suspended particles.

Preferably the composition contains an effective amount of a detergent builder Suitable builders include condensed phosphates, especially sodium tripolyphosphate or, less preferably, sodium pyrophosphate or sodium tetraphosphate, sodium metaphosphate, sodium carbonate, sodium silicate, sodium orthophosphate, sodium citrate, sodium nitrilotriacetate, a phosphonate such as sodium ethylenediamine tetrakis (methylene phosphonate), sodium diethylenetriamine pentakis (methylene phosphonate), sodium aceto diphosphonate or sodium aminotris (methylene phosphonate), sodium ethylenediamine tetraacetate or a zeolite. Other less preferred builders include potassium or lithium analogues of the above sodium salts.

The proportion of builder is typically from about 5% to about 40% by weight of the liquid detergent composition. Usually 10% to 35%, preferably 15–30%, more preferably 18 to 28%, most preferably 20 to 27%. Mixtures of two or more builders are often employed, e.g. sodium tripolyphosphate with sodium silicate and/or sodium carbonate and/or with zeolite; or sodium nitrilotriacetate with sodium citrate.

Preferably the builder is at least partly present as solid particles suspended in the composition.

The invention is also applicable to the preparation of unbuilt cleaning compositions or compositions in which all the builder is present in solution.

The surfactant may be an anionic, nonionic, cationic, amphoteric, zwitterionic and/or semi polar surfactant which may typically be present in concentrations of from 2 to 35% by weight of the composition, preferably 5 to 30%, more usually 7 to 25%, e.g. 10 to 20%.

Usually the composition contains an alkyl benzene sulphonate together with one or more other surfactants such as an alkyl sulphate and/or alkyl polyoxyalkylene sulphate and/or a non-ionic surfactant. The latter may typically be an alkanolamide or a polyoxyalkylated alcohol.

Other anionic surfactants include alkyl sulphates, alkane sulphonates, olefin sulphonates, fatty acid ester sulphonates, soaps, alkyl sulphosuccinates, alkyl sulphosuccinamates, taurides, sarcosinates, isethionates and sulphated polyoxyalkylene equivalents of the aforesaid categories of anionic surfactant.

The cation of the anionic surfactant is preferably sodium but may alternatively be, or comprise, potassium, ammonium, mono-di- or tri $C_{1-4}$ alkyl ammonium or mono-di- or tri- $C_{1-4}$ alkanolammonium, especially ethanolammonium.

The surfactant may be wholly or predominantly non ionic, e.g. a polyoxyalkylated alcohol alone or in admixture with a polyoxyalkylene glycol Other non-ionic surfactants which may be used include polyoxyalkylated derivatives of alkylamines, carboxylic acids, mono or dialkylglycerides, sorbitan esters, or alkylphenols, and alkyloamides. Semipolar surfactants include amine oxides.

All references herein to polyoxyalkylene groups are preferably to polyoxyethylene groups, or less preferably to polyoxypropylene or mixed oxyethylene oxypropylene copolymeric or block copolymeric groups or to such groups with one or more glyceryl groups. Preferably the polyoxyalkylene groups from 1 to 30, more usually 2 to 20, e.g. 3 to 15, especially 3 to 5 alkyleneoxy units.

Cationic surfactants for use according to our invention include quaternised or unquaternised alkylamines, alkylphosphines, or amido amines or imidazolines. Examples include mono- or di- ($C_{8-22}$ alkyl) tri- or di- ($C_{1-4}$ alkyl) ammonium salts, mono ($C_{8-22}$ alkyl) di ($C_{1-4}$ alkyl) mono phenyl or benzyl ammonium salts, alkyl pyridinium, quinolinium or isoquolinium salts, or mono- or bis- ($C_{8-22}$ alkylamidoethyl) amine salts or quaternised derivatives, and the corresponding imidazolines formed by cyclising such amido amines. The anion of the cationic salts may be chloride, sulphate, methosulphate, fluoride, bromide, nitrate, phosphate, formate, acetate, lactate, tartrate, citrate, tetrachloroacetate or any other anion capable of conferring water solubility. Amphoteric surfactants include betaines and sulphobetaines e.g. those formed by quaternising any of the aforesaid cationic surfactants with chloroacetic acid.

In every case the surfactant for use herein has an alkyl group with an average of from 8 to 22 preferably 10 to 20, e.g. 12 to 18 carbon atoms. Alkyl groups are preferably primary and straight chain, however we do not exclude branched chain or secondary alkyl groups. In the case of alcohol based non-ionics the branched chain are sometimes preferred.

In general any surfactant referred to in GB 1,123,846, or in "Surface Active Agents and Detergents" by Schwartz, Perry and Berch, may be used.

Preferably the pH of the liquid detergent composition is alkaline, e.g. above 7.5, especially 7.5 to 12 typically 8 to 11, e.g. 9 to 10.5.

The liquid detergent composition contains dissolved, surfactant-desolubilising electrolyte. This may comprise a dissolved portion of the builder and/or any other salt, inorganic or organic, which is not itself a surfactant and which salts out the encapsulant, and also preferably the surfactants present, from solution (including micellar solution). Examples include sodium chloride, sodium nitrate, sodium bromide, sodium iodide, sodium fluoride, sodium borate, sodium formate, or sodium acetate, or corresponding potassium salts. Preferably, however, the electrolyte is a salt which is required to perform a useful function in the wash liquor. The selection of electrolyte will to some extent depend on the encapsulant and the surfactant, since certain of the above electrolytes may desolubilise some compounds but not others.

The electrolyte may comprise sodium sulphate in minor concentrations, but electrolyte mixtures containing concentrations of sodium sulphate of about 3% or over based on the total weight of the detergent composition, are preferably not used because they may give rise to undesirable crystallization on standing.

The amount of dissolved electrolyte needed to provide a suspending structure depends upon the nature and amount of surfactant present as well as the capacity of the electrolyte to salt out the surfactant. The greater the concentration of surfactant, and the more readily it is salted out by the electrolyte in question, the less the amount of electrolyte which is required. Generally, concentrations of electrolyte in solution of greater than 3%, more usually greater than 5% by weight, are required, typically 6 to 20%, especially 7 to 19%, preferably 8 to 18%, more preferably 9 to 17%, most preferably 10 to 16%, e.g. 11 to 15% by weight of electrolyte in solution, based on the weight of the composition, or enough to contribute at least 0.5, preferably at least 1.0 more preferably at least 1.5, most preferably from 2 to 4.5 gm ions of alkali metal per litre to the aqueous phase left after any suspended solid has been separated e.g. by centrifuging.

In order to determine the optimum amount of electrolyte required for a particular formulation any one or more of a number of indications may be employed. The concentration of dissolved electrolyte may be raised progressively in an aqueous surfactant, until the electrical conductivity falls to a minimum with addition of more electrolyte and a stable, turbid, spherulitic system is observed. The amount of electrolyte may then be optimised within this region by preparing samples with different concentrations of electrolyte in the region of the conductivity minimum and centrifuging for 90 minutes at 20,000 G until a concentration is identified at which no clear lye phase separates.

The electrolyte content is preferably .adjusted to provide at least three months storage stability at ambient, at 0.C. and at 40° C. Behaviour on shearing is another characteristic which is controllable by adjusting the electrolyte concentration Where the concentration is too low the formulations, all of which are usually thixotropic, tend not only to become less viscous with increasing shear, but to retain the greater fluidity after the applied shear has been withdrawn instead of reverting to their original higher viscosity. Such formulations are often unstable after shearing thus they may undergo separation after high shear mixing, centrifugal deaeration, or high speed bottling. Increasing the concentration of dissolved electrolyte will generally avoid such shear instability by providing a more robust structure.

Electrolyte concentrations just above the minimum required to prevent shear instability sometimes cause the opposite problem. After shearing, the viscosity of the composition recovers to a higher value than that before shearing. This can result in the composition becoming too viscous after being agitated or shaken This problem too can usually be cured by increasing the electrolyte content.

If difficulty is encountered obtaining a stable spherulitic composition the concentration of surfactant may be increased, or the proportion of less "soluble" surfactant raised, e.g. increasing the amount of sodium alkyl benzene sulphonate or of low HLB non-ionic surfactant, i.e. having an HLB less than 12, preferably less than 10 e.g. less than 8 more usually 2 to 5.

Alternatively, if larger concentrations of electrolyte are used a lamellar, G-phase or hydrated solid structure may be obtained. This may be obtained for any desired detergent surfactant or surfactant mixture by adding enough electrolyte to salt out the surfactant so that the majority is centrifuged off at 800 g leaving a clear lye phase. If the composition is then not sufficiently stable to storage, it may be rendered non-sedimenting by decreasing the proportion of water. Alternatively if the composition obtained in this way is not mobile it may be progressively diluted with water until it is capable of being poured, or until an optimum balance of mobility and stability has been struck.

Additionally, but less preferably, our invention covers liquid detergent compositions having suspending power which is provided or contributed to by components other than the salted out surfactants, e.g. high concentrations of carboxymethyl cellulose or the presence of poly electrolyte dispersants, soluble gums or emulsifiers or bentonite.

The detergent composition may contain any of the usual minor ingredients such as soil suspending agents (e.g. carboxymethyl cellulose), preservatives such as formaldehyde or tetrakis (hydroxymethyl) phosphonium salts, bentonite clays, or any of the enzymes described herein, protected according to the invention. Where a bleach is to be employed it may be convenient to encapsulate the bleach e.g. with a hydrophilic encapsulant, or in ahydrophobic medium, such as, for instance a silicone or hydrocarbon as described in EP-A-0238216 or GB-A-2200377.

Particularly preferred liquid detergents are those containing: long chain (e.g. $C_{10-14}$) linear alkyl benzene sulphonates in an amount of 5-12%, long chain alkyl, or alkyl ether, sulphates, e.g. with 0-5 ethyleneoxy units, in an amount of 0-3%; fatty acid alkanolamides, and/or alcohol ethoxylates having HLB of less than 12 in an amount of 1-5%; mixtures of mono-and di-long chain alkyl phosphates in an amount of 0-3%, e.g. 0.1-1%; sodium tripolyphosphate (preferably prehydrated with from 0.5 to 5% by weight of water) in an amount of 14-30%, e.g. 14-18% or 20-30%; optionally sodium carbonate in an amount of up to 10%, e.g. 5-10% with the total of sodium tripolyphosphate and carbonate being preferably 20-30%; antiredeposition agents such as sodium carboxymethyl cellulose in an amount of 0.05-0.5%; optical brightening agents in an amount of 0.05-0.5%; chelating agents, e.g. amino phosphonates such as methylene phosphonates of di- and polyamines, especially sodium ethylenediamine tetra[- methylene phosphonate] or dithylene triamine hexa[-methylene phosphonate] optionally present in an amount of 0.1-15%; together with conventional minor additives such as perfume colouring preservatives, the remainder being water, the percentages being by weight of the total liquid detergent. The liquid detergent may have a pH after dilution to 1% of 6 to 13, preferably 7 to 12, more usually 8 to 11, e.g. 9 to 10.5.

The invention is by no means exclusively applicable to the preparation of laundry detergents. Any liquid aqueous surfactant system in which particulate additives can be suspended and which require the presence of enzymes which are chemically incompatible with the aqueous surfactant medium may be prepared according to the invention. For example enzymes, especially proteases, lipases and amylases are useful in dish washing detergents, both for manual and automatic use.

EXAMPLES

The invention will be illustrated by the following examples in which all storage tests were performed at 30.C, unless otherwise noted.

EXAMPLE 1

2 parts by weight of a 2% protease solution in an 80:20 wt/wt mixture of propylene glycol and water, having an activity of 8,000 Novo Protease Units gm31 1, sold by NovoNordisk A/S under the registered trademark ESPERASE, 8.0 L, and one part by weight of a 4% by weight aqueous solution of polyvinyl alcohol having a mean molecular weight of 80,000-100,000 and being 88% hydrolysed were mixed to give a clear mobile liquid which was stable to storage.

The enzyme/P.V.A-containing liquid was added to a liquid detergent formulation to give a final composition.:

| | wt % |
|---|---|
| Sodium linear $C_{12-14}$ alkylbenzene sulphonate | 9.3% |
| Sodium linear $C_{12-18}$ alkyl 3 mole ethoxy sulphate | 1.85% |
| Coconut diethanolamide | 1.85% |
| Sodium tripolyphosphate | 16.7% |
| Sodium carbonate | 6.7% |
| Sodium carboxymethylcellulose | 0.9% |
| Optical brightening agent | 0.1% |
| Enzyme/PVA solution | 3.0% |
| Water | balance |
| pH | 10.5% |

After two weeks storage the stain removing power of the above formulation was superior to that of a control formulation containing a silicone protected enzyme at equivalent initial protease activity.

EXAMPLE 2

ESPERASE 8.0 L protease solution was mixed with various aqueous polymers.

The mixtures were added to a liquid detergent formulation comprising:

| | |
|---|---|
| sodium $C_{10-14}$ linear alkyl benzene sulphonate | 6.0% |
| triethanolamine $C_{12-14}$ alkyl sulphate | 1.5% |
| $C_{12-13}$ alkyl 3 mole ethoxylate | 2.0% |
| sodium tripolyphosphate | 25.0% |
| sodium ethylenediamine tetrakis (methylene phosphonate) | 0.5% |
| Optical brightener | 0.2% |
| Silicone antifoam | 0.2% |
| sodium carboxymethyl cellulose | 0.1% |
| perfume | 0.2% |
| formaldehyde | 0.05% |

Enzyme activity was determined by comparing soil and stain removal with that of an enzyme free, control formulation.

The retention of activity after storage was the percentage improvement after storage compared with the control, expressed as a percentage based on the percentage improvement of the freshly prepared sample.

The results are indicated in the following table:

| Polymer added | weight ratio enzyme solution: polymer solution | % by weight additive system added to detergent | % residual performance | % residual performance |
|---|---|---|---|---|
| 4% aqueous P.V.A. MW 80,000-100,000 88% hydrolysed | 2:1 | 0.5% | 73% after 21 days | 47% after 23 days |
| 4% polyvinyl pyrrolidone MW 700,000 | 2:1 | 0.5% | 100% after 21 days | 85% after 151 days |
| 4% aqueous gelatin | 2:1 | 0.5% | 60% after 21 days | 53% after 26 days |
| 1% "Emulgum," 200 guar gum | 1:2 | 1% | 64% after 17 days | |
| 1% "Emulgum," 200 S guar gum | 1:2 | 1% | 77% after 21 days | |
| None | — | 0.33% | 69% after 15 days | 31% after 50 days |

The final result in the above table was obtained using "ESPERASE" 8.0 L without added polymer. The percentage retention appeared remarkable for an unprotected enzyme, and contradicted earlier results obtained with other unprotected enzyme systems in which activity was lost totally after 2 to 3 days.

It was noted, however, that the particular sample of liquid enzyme used in the above experiment contained about 2% of adventitious carbohydrate which may have functioned as a stabilizing polymer in accordance with our invention and to which the high retention of activity of the "unprotected" sample has now been ascribed.

The performance of polyvinyl pyrrolidone was especially marked.

EXAMPLE 3

Example 2 was repeated using 8 different PVA compositions. The detergent samples were tested at intervals and the stain removal compared with that of a detergent containing a commercial silicone protected enzyme according to our EP-A-0238216, and a non-enzymatic control.

The % retention of the activity of the enzymatic formulations, compared with the non-enzymatic formulation is recorded in Table 2.

TABLE 2

| Encapsulant | MW | % hydrolysis | % retention of activity after: 2 weeks | 4 weeks | 8 weeks |
|---|---|---|---|---|---|
| PVA | 3,000 | 75 | 82 | 64 | 64 |
| PVA | 2,000 | 75 | 84 | 58 | — |
| PVA | 10,000 | 88 | 88 | 70 | 64 |
| PVA | 90,000 | 88 | 83 | 72 | 61 |
| PVA | 125,000 | 88 | 82 | 70 | 64 |
| PVA | 95,000 | 96 | 81 | 56 | 50 |
| PVA | 16,000 | 98 | 88 | 58 | 53 |
| PVA | 88,000 | 98 | 70 | 58 | 41 |
| PVA | 126,000 | 98 | 92 | 64 | 50 |
| PVA | 14,000 | 100 | 72 | 39 | — |
| PVA | 155,000 | 100 | 78 | 39 | — |
| Silicone | | | 58 | 35 | 23 |

The results indicate that the more sparingly soluble PVA polymers having a degree of hydrolysis less than 90% are more effective then the polymers which are more soluble than 90% hydrolysed PVA.

EXAMPLE 4

Acetone precipitated PVP-protease was prepared as follows: 15 g of polyvinyl pyrrolidone having a mean molecular weight of about 38,000 was dissolved in 150 ml of a 2% protease solution with about 10% total dry substance prepared according to U.S. Pat. No. 3,723,250 and sold by Novo-Nordisk A/S under the registered trade mark "SAVINASE" to give a clear solution 300 ml of acetone was added slowly with vigorous stirring, causing precipitation and heating from room temperature to about 30°-35° C. The dispersion was left with stirring for 10-15 minutes and then filtered on a Buchner funnel, washed with acetone, sucked dry and left to air dry. The PVP:protease ratio was calculated as 5.

Salt precipitated PVP-protease was prepared as follows: 2 g of PVP (MW 38,000) was dissolved in 22 g of SAVINASE solution. The solution was heated to 35° C., and 6 g of sodium sulphate was added slowly with vigorous stirring., causing precipitation. The suspension was filtered and air dried. The PVP:protease ratio was 2.5.

2% of each PVP-protease sample was added to the detergent of Example 1 instead of the Enzyme/PVA at a level of 0.05 KNPU/$g^{-1}$. The protease activity was measured before and after storage as follows (% residual activity). Unprotected powder protease was used as reference

| Ratio | Prcpt. | 0 days | 3 d | 7 d | 14 d | 21 d |
|---|---|---|---|---|---|---|
| 5 | acetone | 100 | 88.3 | 79.2 | 70.3 | 58.8 |
| 2.5 | salt | 100 | 85.7 | 73.2 | 56.9 | 37.9 |
| 0 | reference | 100 | 83.3 | 61.5 | 34.0 | 16.5 |

It is seen that samples prepared according to the invention provide substantial stabilization.

EXAMPLE 5

Samples of salt precipitated PVP-protease were prepared as in Example 4, but with varying PVP:protease ratio and PVP molecular weight, as indicated below.

A spray dried PVP-protease sample was prepared as follows: 226 g of PVP was dissolved in 26 kg of a 7% protease solution (Savinase), pH was adjusted to 6.5 (dilute sulfuric acid), and the solution was spray dried on a Standard Unit 1 from A/S Niro Atomizer with the atomizing wheel at 2000 rpm and with an air through-put of approx. 1000 cubic meters per hour. The air temperature was inlet 170° C. and outlet 65° C. The spray dried product contained 17 % of protease.

All samples were tested by storage tests as in Example 4. A protease solution was included as reference.

| Method | MW | PVP:enz | 0 days | 3 d | 7 d | 14 d | 28 d |
|---|---|---|---|---|---|---|---|
| Salt | 38,000 | 0.75 | 100 | 63.7 | 49.7 | 35.5 | 21.5 |
| " | " | 0.5 | 100 | 64.2 | 51.7 | 41.9 | 28.3 |
| " | " | 0.25 | 100 | 59.8 | 45.1 | 34.7 | 22.2 |
| " | " | 0.033 | 100 | 33.3 | 14.5 | 7.8 | 4.8 |
| " | 630,000 | 0.033 | 100 | 30.8 | 12.8 | 8.3 | 5.4 |
| Spray | 38,000 | 0.125 | 100 | 75.8 | 55.8 | 41.4 | 22.9 |
| Reference | | 0 | 100 | 15.3 | 4.9 | 0.0 | 0.0 |

It is seen that the inventoin provides stabilization even at dosages as low as polymer:enzyme=0.0331:1 with both molecular weights tested. Increasing amounts of PVP provide increasing stabilization. Enzyme Preparations made by spray drying and by salt precipitation appear to provide a similar degree of stabilization.

EXAMPLE 6

Detergent containing PVP (MW 700,000) and protease was prepared and tested as in Example 1. The type of protease and the enzyme dosage in the detergent are indicated below; a 5% protease solution was used in the case of Alcalase. Washing tests were made before and after storage with standard soiled cloths EMPA 116 and 117, and results express residual % washing performance after 56 days storage. Liquid proteases without PVP were used as references.

| Protease | PVP | Dosage | % retention |
|---|---|---|---|
| Esperase | + | .375% | 77% |
| " | − | .25% | 17% |
| Alcalase | + | .375% | 73% |
| " | + | .15% | 55% |
| " | − | .25% | 23% |
| " | − | .10% | 17% |
| Savinase | + | .375% | 71% |
| " | + | .1875% | 58% |
| " | − | .125% | 0% |

EXAMPLE 7

The experiment in Example 6 was repeated with Alcalase and varying ratios PVP;protease. The enzyme dosage in the detergent was 0.28% in each case. Liquid Alcalase was used as reference.

| PVP:protease | % retention |
|---|---|
| 0 (reference) | 0% |
| .016 | 38% |
| .08 | 62% |
| .4 | 56% |

-continued

| PVP:protease | % retention |
|---|---|
| 1 | 60% |

Stabilization according to the invention is observed even with extremely low amounts of PVP.

EXAMPLE 8

This experiment was similar to Example 7, but the order of mixing was varied. In each case 0.28% of a 5% Alcalase solution and 0.14% of a 4% PVP solution were added (PVP: protease=0.4). In one case the two solutions were premixed before adding to the detergent (as in Example 7); in another case PVP was added first, then protease; and in yet another first protease, then PVP. In the reference, PVP was omitted.

Enzyme stabilization was observed both in the case of coprecipitation, in the case of contacting dispersed PVp with dissolved protease and in the case of contacting dissolved PVP with dispersed protease.

We claim:

1. A method for preparing a stabilized enzyme dispersion, comprising:

(1) precipitating a water-soluble polymer from a single phase, aqueous solution to form an aqueous dispersion, and (2) before, simultaneously with or after precipitating the polymer, contacting the dissolved or dispersed polymer with an aqueous solution or fine aqueous dispersion of an enzyme without any covalent bonding between the polymer and the enzyme.

2. The method according to claim 1, wherein said enzyme is selected from the group consisting of a protease, amylase, cellulase and lipase.

3. The method according to claim 1, wherein said polymer is selected from the group consisting of polyvinyl alcohol, polyvinyl pyrrolidone, poly-$C_{1-4}$ carboxylic acid salt, carboxymethyl cellulose salt, gelatin and guar gum.

4. The method according to claim 1, wherein said polymer is a partially hydrolyzed polyvinyl ester of a $C_{1-4}$ carboxylic acid having a degree of hydrolysis of from 25 to 90%.

5. The method according to claim 3, wherein said polyvinyl pyrrolidone has an average molecular weight in the range of about 1,000 to 1,500,000.

6. The method according to claim 1, wherein the weight ratio of said polymer to said enzyme is in the range of 0.03 to 5.

7. The method according to claim 1, wherein the polymer is precipitated by contacting with an effective amount of a precipitant.

8. The method according to claim 7, wherein the precipitant is an electrolyte or an organic solvent.

9. The method according to claim 8, wherein said electrolyte is selected from the group consisting of sodium sulphate, sodium citrate, sodium tripolyphosphate, sodium carbonate and ammonium sulphate.

10. The method according to claim 8, wherein said organic solvent is acetone or ethanol.

11. The method according to claim 1, wherein the polymer is precipitated by evaporation.

12. The method according to claim 1, wherein precipitation of said enzyme occurs simultaneously with precipitation of said polymer.

13. The method according to claim 12, wherein a solution containing said polymer and said enzyme is contacted with a precipitant to directly form an enzyme dispersion.

14. The method according to claim 12, wherein a finely divided coprecipitate of the enzyme and polymer is dispersed in water.

15. The method according to claim 1, wherein the precipitated, dispersed polymer is contacted with the dissolved enzyme.

16. The method according to claim 1, wherein the dissolved polymer is contacted with the finely divided solid enzyme.

17. The method according to claim 12, in which a clear solution comprising polyvinyl pyrrolidone and an enzyme selected from the group consisting of a protease, an amylase, a cellulase and a lipase if employed as the single-phase solution.

* * * * *